United States Patent
Knappe et al.

(10) Patent No.: US 10,143,637 B2
(45) Date of Patent: Dec. 4, 2018

(54) LONGER-HOLDING HAIRSPRAY

(71) Applicant: Henkel AG & Co. KGaA, Duesseldorf (DE)

(72) Inventors: Thorsten Knappe, Schenefeld (DE); Susanne Schmarje, Hamburg (DE)

(73) Assignee: Henkel AG & Co. KGaA (DE)

( * ) Notice: Subject to any disclaimer, the term of this patent is extended or adjusted under 35 U.S.C. 154(b) by 93 days.

(21) Appl. No.: 15/151,604

(22) Filed: May 11, 2016

(65) Prior Publication Data

US 2016/0250120 A1    Sep. 1, 2016

Related U.S. Application Data

(63) Continuation of application No. PCT/DE2014/200435, filed on Sep. 1, 2014.

(30) Foreign Application Priority Data

Dec. 4, 2013 (DE) .................. 10 2013 224 869

(51) Int. Cl.

| | |
|---|---|
| *A61K 8/37* | (2006.01) |
| *A61K 8/39* | (2006.01) |
| *A61K 8/31* | (2006.01) |
| *A61K 8/33* | (2006.01) |
| *A61Q 5/06* | (2006.01) |
| *A61K 8/81* | (2006.01) |
| *A61K 8/04* | (2006.01) |
| *A61K 8/73* | (2006.01) |

(52) U.S. Cl.
CPC ............... *A61K 8/37* (2013.01); *A61K 8/046* (2013.01); *A61K 8/31* (2013.01); *A61K 8/33* (2013.01); *A61K 8/39* (2013.01); *A61K 8/731* (2013.01); *A61K 8/736* (2013.01); *A61K 8/817* (2013.01); *A61K 8/8158* (2013.01); *A61K 8/8176* (2013.01); *A61K 8/8182* (2013.01); *A61Q 5/06* (2013.01); *A61K 2800/54* (2013.01); *A61K 2800/59* (2013.01)

(58) Field of Classification Search
None
See application file for complete search history.

(56) References Cited

U.S. PATENT DOCUMENTS 8,309,066 B2 * 11/2012 Taden .................. C08G 73/02
424/70.11

FOREIGN PATENT DOCUMENTS

| | | | |
|---|---|---|---|
| DE | 102009003032 | * | 11/2010 |
| WO | 2010/122286 A2 | | 10/2010 |

OTHER PUBLICATIONS

Eaton et al., Achieving silicone-like feel without silicones,Speciality Chemicals Magazine, 31(3), 25-26. ABS. (Year: 2011).*
PCT International Search Report (PCT/DE2014/200435) dated Nov. 12, 2014.
Gao et al., "Study of Hair Shine and Hair Surface Smoothness", Journal of Cosmetic Science, XP002733643, vol. 60, pp. 187-197, 2009.

* cited by examiner

*Primary Examiner* — Alton N Pryor
(74) *Attorney, Agent, or Firm* — P. Scott Smith

(57) ABSTRACT

The invention relates to hair sprays comprising a pressurized container and an aerosol composition, located therein, which includes, based on its weight, 20 to 80% by weight of at least one propellant, 0.1 to 20% by weight of at least one fixing polymer, and 0.01 to 5% by weight of esters of the formula (I), in which R1 stands for —H or —CH3, R2 for a straight-chain or branched alkyl group having 7 to 15 carbon atoms, and n for an integer from the group comprising 1, 2, 3, 4, 5, 6, 7, 8; the hair sprays bring about an improved hair feel, improved lightness of the hairstyle, and improved hair texture, also with further improvement of the hold.

13 Claims, No Drawings

LONGER-HOLDING HAIRSPRAY

FIELD OF THE INVENTION

The present invention generally relates to a ready-to-use formulated preparation for the treatment of keratinic fibers, particularly human hair, in the form of a spray, and the use of said preparation for the treatment of keratinic fibers, particularly human hair.

BACKGROUND OF THE INVENTION

Hair sprays typically include synthetic polymers as the styling component. Preparations including a dissolved or dispersed polymer can be applied to the hair by means of propellant gases or by a pump mechanism.

The polymer(s) is (are) used to give the hairstyle the longest possible hold. This hairstyle stability is often accompanied by a loss of hair feel; i.e., the hair loses its softness and its pleasant texture, whereby in the extreme case a feeling of a "helmet-like" hairstyle results.

However, in addition to a high degree of hold, styling agents should satisfy a wide range of further requirements. These can be divided roughly into properties on the hair, properties of the particular formulation, e.g., properties of the foam, gel, or sprayed aerosol, and properties related to the handling of the styling agent, particular importance being attached to the properties on the hair. Mention can be made in particular of humidity resistance, low tackiness, and a balanced conditioning effect. Furthermore, if possible, a styling agent should be universally suitable for all hair types.

The present invention was based on the object of providing hair sprays which give the hair a pleasant texture and a well-groomed hair feel, without the long-lasting hold being negatively affected. In the ideal case, even an improvement of the hold is to be achieved.

It has now been found that the hair feel, the lightness of the hairstyle, and the hair texture can also be improved with a further improvement of the hold, if certain esters are incorporated into the hair spray.

Furthermore, other desirable features and characteristics of the present invention will become apparent from the subsequent detailed description of the invention and the appended claims, taken in conjunction with this background of the invention.

BRIEF SUMMARY OF THE INVENTION

A hair spray, comprising a pressurized container and, located therein, an aerosol composition, which includes, based on its weight, 20 to 80% by weight of at least one propellant, 0.1 to 20% by weight of at least one fixing polymer, and 0.01 to 5% by weight of esters of the formula (I)

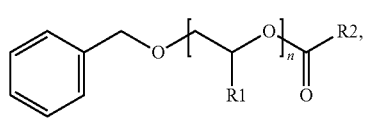

in which R1 stands for —H or —CH$_3$, R2 for a straight-chain or branched alkyl group having 7 to 15 carbon atoms, and n for an integer from the group comprising 1, 2, 3, 4, 5, 6, 7, 8.

A method for styling hair, characterized in that an aerosol composition including esters of the formula (I)

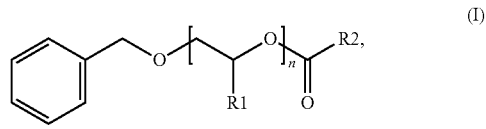

in which R1 stands for —H or —CH$_3$, R2 for a straight-chain or branched alkyl group having 7 to 15 carbon atoms, and n for an integer from the group comprising 1, 2, 3, 4, 5, 6, 7, 8, is applied to keratinic fibers by means of a propellant or a propellant mixture from a pressurized container.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the invention is a hair spray, comprising a pressurized container and, located therein, an aerosol composition, which, based on its weight, includes
a) 20 to 80% by weight of at least one propellant,
b) 0.1 to 20% by weight of at least one fixing polymer,
c) 0.01 to 5% by weight of esters of the formula (I)

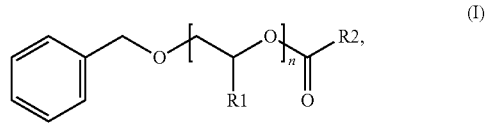

in which
R1 stands for —H or —CH$_3$,
R2 for a straight-chain or branched alkyl group having 7 to 15 carbon atoms, and
n for an integer from the group comprising 1, 2, 3, 4, 5, 6, 7, 8.

The hair spray compositions of the invention include as the first essential component 20 to 80% by weight of at least one propellant.

Propellants (propellant gases) suitable according to the invention are, for example, propane, n-butane, isobutane, dimethyl ether (DME), nitrogen, air, laughing gas, and 1,1-difluoroethane, namely, both individually and in combination. Hydrophilic propellant gases such as, e.g., carbon dioxide, can also be used advantageously within the context of the present invention, if the proportion of hydrophilic gases is selected as low and a lipophilic propellant gas (e.g., propane/butane) is present in excess. Dimethyl ether, propane, n-butane, isobutane, and mixtures of said propellant gases are particularly preferred. Very especially preferred is the use of propane/butane mixtures or isobutane.

Particularly preferred hair sprays of the invention are characterized in that the aerosol composition includes, based on its weight, 20 to 80% by weight, preferably 22.5 to 77.5% by weight, more preferably 25 to 75% by weight, even more preferably 27.5 to 72.5% by weight, and particularly 30 to 70% by weight of a propellant or propellant mixture, selected from dimethyl ether, HFO1234yf, HFO1234ze, propane, propene, n-butane, isobutane, isobutene, n-pentane, pentene, isopentane, and isopentene, or mixtures thereof.

The propellant is advantageously selected so that it can serve simultaneously as a solvent for other ingredients such as, for example, oil and wax components, the fatty substances (D). The propellant can then be used as a solvent for these last-mentioned components, if they are soluble in the propellant to at least 0.5% by weight at 20° C., based on the propellant.

According to a preferred embodiment, the preparations of the invention include the aforesaid hydrocarbons, dimethyl ether, or mixtures of the aforesaid hydrocarbons with dimethyl ether as the sole propellant. The invention, however, also expressly comprises the concurrent use of propellants of the chlorofluorocarbon type, but particularly fluorocarbons.

Very particularly preferred combinations of the invention are characterized in that the propellant-containing hair treatment agent includes, based on its weight, 7.5 to 57.5% by weight, preferably 10 to 55% by weight, more preferably 15 to 52.5% by weight, even more preferably 17.5 to 55% by weight, particularly preferably 20 to 50% by weight, and particularly 25 to 45% by weight of at least one propellant, selected from n-propane, n-butane, isobutane, n-pentane, dimethyl ether, and mixtures thereof.

The hair spray compositions of the invention include as a second essential component 0.1 to 20% by weight of at least one fixing polymer.

In this case, these film-forming and/or fixing polymers can be cationic, anionic, nonionic, or amphoteric both permanently and also temporarily. The present invention furthermore also comprises the realization that when at least two film-forming and/or fixing polymers are used, these can of course have different charges. It can be preferred according to the invention if an ionic film-forming and/or fixing polymer is used together with an amphoteric and/or nonionic film-forming and/or fixing polymer. The use of at least two oppositely charged film-forming and/or fixing polymers is also preferred. In the last case, a special embodiment can in turn include in addition at least one other amphoteric and/or nonionic film-forming and/or fixing polymer.

Because polymers are often multifunctional, their functions cannot always be differentiated from each other clearly and unambiguously. This applies in particular to film-forming and fixing polymers. Nevertheless, some film-forming polymers will be described by way of example. It will be pointed out explicitly at this point, however, that both film-forming and fixing polymers are essential within the scope of the present invention. Because both properties are also not completely independent of one another, the term "fixing polymers" is also always understood to mean "film-forming polymers" and vice versa.

The preferred properties of the film-forming polymers include film formation. Film-forming polymers are understood to be such polymers that upon drying leave behind a continuous film on the skin, hair, or nails. Such film formers can be used in very different cosmetic products such as, for example, facial masks, makeup, hair setting products, hair sprays, hair gels, hair waxes, hair treatments, shampoos, or nail polish. Polymers preferred in particular are those that have a sufficient solubility in alcohol or water/alcohol mixtures, in order to be present in the agent of the invention in completely dissolved form. The film-forming polymers can be synthetic or natural in origin.

According to the invention, film-forming polymers are understood further to be such polymers that are capable of depositing a transparent polymer film on hair when used in 0.01 to 20% by weight aqueous, alcoholic, or aqueous/alcoholic solution. The film-forming polymers in this case can be charged in an anionic, amphoteric, nonionic, permanently cationic, or temporarily cationic fashion.

Suitable synthetic, film-forming, hair-fixing polymers are homopolymers or copolymers, made up of at least one of the following monomers: vinylpyrrolidone, vinylcaprolactam, vinyl esters such as, e.g., vinyl acetate, vinyl alcohol, acrylamide, methacrylamide, alkyl and dialkyl acrylamide, alkyl and dialkyl methacrylamide, alkyl acrylate, alkyl methacrylate, propylene glycol, or ethylene glycol, whereby the alkyl groups of said monomers are preferably $C_1$ to $C_7$ alkyl groups, particularly preferably $C_1$ to $C_3$ alkyl groups.

Homopolymers of vinylcaprolactam, vinylpyrrolidone, or N-vinylformamide are mentioned by way of example. Other suitable synthetic film-forming, hair-fixing polymers are, e.g., copolymers of vinylpyrrolidone and vinyl acetate, terpolymers of vinylpyrrolidone, vinyl acetate, and vinyl propionate, polyacrylamides, which are marketed, for example, under the trade names Akypomine® P 191 by the company CHEM-Y, Emmerich, or Sepigel® 305 by the company Seppic; polyvinyl alcohols, which are marketed, for example, under the trade names Elvanol® by Du Pont or Vinol® 523/540 by the company Air Products; and polyethylene glycol/polypropylene glycol copolymers, which are marketed, for example, under the trade names Ucon® by Union Carbide.

Suitable natural film-forming polymers are, e.g., cellulose derivatives, e.g., hydroxypropyl cellulose with a molecular weight of 30,000 to 50,000 g/mol, which is marketed, for example, under the trade name Nisso SI® by the company Lehmann & Voss, Hamburg.

Fixing polymers contribute to maintaining and/or building up the hair volume and hair fullness of the overall hairstyle. These so-called fixing polymers are simultaneously also film-forming polymers and therefore generally typical substances for styling hair treatment products such as hair setting products, hair mousses, hair waxes, and hair sprays. The film formation in this case can occur at points and only connect a few fibers to one another.

Substances, which furthermore impart hydrophobic properties to the hair, are preferred in this case, because they reduce the hair's tendency to absorb moisture, therefore water. As a result, the limp drooping of hair strands is reduced and thus a long-lasting structure and hold for the hairstyle are ensured. The so-called curl retention test is often used as a test method for this. These polymeric substances can be incorporated furthermore successfully into leave-on and rinse-off hair conditioners or shampoos. Because polymers are frequently multifunctional, i.e., exhibit multiple effects desirable in terms of application technology, many polymers are placed in a number of groups classified by mode of action, as is also the case in the CTFA Handbook. Due to the significance of the fixing polymers, they should therefore be listed explicitly in the form of their INCI names. The aforesaid film-forming polymers, of course, are therefore also found in this list of polymers to be used preferably according to the invention.

Examples of common film-forming, fixing polymers are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, *Bacillus*/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, and Yeast Palmitate.

An especially pronounced improvement of the hairstyle hold can be achieved, if a film-forming and/or fixing polymer is used, which forms brittle, hard polymer films. Preferably, therefore, suitable film-forming and/or fixing polymers are used. Preferably, the agent of the invention therefore includes at least one film-forming and/or fixing polymer selected from aminomethyl propanol salts of copolymers of allyl methacrylate with one or more monomers selected from acrylic acid, methacrylic acid, acrylic acid esters, and methacrylic acid esters, vinylpyrrolidone/vinyl acetate copolymers, vinylpyrrolidone/vinylcaprolactam/dimethylaminopropyl-acrylamide copolymers, copolymers of octylacrylamide with t-butylaminoethyl methacrylate and two or more monomers selected from acrylic acid, methacrylic acid, acrylic acid esters, and methacrylic acid esters, and copolymers of $C_{1-2}$-alkyl succinates with hydroxyalkyl acrylates and one or more monomers selected from acrylic acid, methacrylic acid, acrylic acid esters, and methacrylic acid esters.

Suitable film-forming and/or fixing polymers are commercially available.

Particularly preferably, the agent of the invention includes as a film-forming and/or fixing polymer an aminomethyl propanol salt of a copolymer of allyl methacrylate with one or more monomers, selected from acrylic acid, methacrylic acid, acrylic acid esters, and methacrylic acid esters.

Preferably, the aforesaid acrylic acid esters and methacrylic acid esters are $C_1$-$C_{12}$ alkyl acrylates and $C_1$-$C_{12}$ alkyl methacrylates, particularly preferably methyl acrylate, ethyl acrylate, propyl acrylate, methyl methacrylate, ethyl methacrylate, propyl methacrylate, and mixtures thereof.

The copolymer with the INCI name AMP-Acrylates/Allyl Methacrylate Copolymer, which is marketed by the company Noveon under the name Fixate™ G-100, is used preferably as the aminomethyl propanol salt of copolymers of allyl methacrylate with one or more monomers selected from acrylic acid, methacrylic acid, acrylic acid esters, and methacrylic acid esters. The agent of the invention includes said copolymer with very particularly preference.

A preferred vinylpyrrolidone/vinyl acetate copolymer is the PVP/VA Copolymer 60-40 W (INCI name: VP/VA Copolymer, Aqua, Laurtrimonium Chloride).

The copolymer, obtainable from ISP under the name Aquaflex SF 40, with the INCI name VP/Vinyl Caprolactam/DMAPA Acrylates Copolymer is used preferably as the vinylpyrrolidone/vinylcaprolactam/dimethylaminopropylacrylamide copolymer.

A preferred copolymer of octylacrylamide with t-butylaminoethyl methacrylate and two or more monomers selected from acrylic acid, methacrylic acid, acrylic acid esters, and methacrylic acid esters, is the copolymer, obtainable from National Starch under the name Amphomer®, with the INCI name Octylacrylamide/Acrylates Butylaminoethyl Methacrylates Copolymer.

The copolymer, obtainable from ISP under the name Allianz™ LT 120, with the INCI name Acrylates/C1-2 Succinates/Hydroxyacrylates Copolymer is preferred as a copolymer of $C_{1-2}$ alkyl succinates with hydroxyalkylacrylates and one or more monomers selected from acrylic acid, methacrylic acid, acrylic acid esters, and methacrylic acid esters. Hair sprays particularly preferred according to the invention are characterized in that the aerosol composition includes, based on its weight, fixing polymer(s) in a total amount of 0.2% by weight to 17.5% by weight, preferably of 0.5% by weight to 15% by weight, particularly preferably of 2.0% by weight to 10.0% by weight, and particularly of 3.0 to 5.0% by weight, based in each case on the weight of the agent. Very particularly preferred hair sprays of the invention are characterized in that the aerosol composition includes at least one fixing polymer selected from nonionic polymers based on ethylenically unsaturated monomers, particularly from
    homopolymers of N-vinylpyrrolidone,
    nonionic copolymers of N-vinylpyrrolidone,
    homopolymers and nonionic copolymers of N-vinylcaprolactam,
    copolymers of (meth)acrylamide,
    polyvinyl alcohol, polyvinyl acetate,
    chitosan and chitosan derivatives,
    cationic cellulose derivatives,
    cationic copolymers of 3-($C_1$ to $C_6$)-alkyl-1-vinyl imidazolinium,
    homopolymers and copolymers including the structural unit of the formula (M-1)

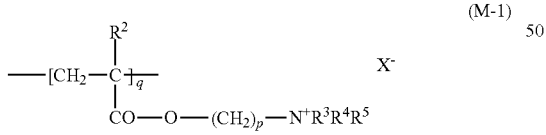

in which $R^2$=—H or —$CH_3$, $R^3$, $R^4$, and $R^5$ independently of one another are selected from ($C_1$ to $C_4$) alkyl, ($C_1$ to $C_4$) alkenyl, or ($C_2$ to $C_4$) hydroxyalkyl groups, p=1, 2, 3, or 4, q is a natural number, and $X^-$ is a physiologically acceptable organic or inorganic anion, anionic polymers, which have carboxylate and/or sulfonate groups, and
    anionic polyurethanes.

It turned out that a certain copolymer in the combination of the invention provides exceptionally good degrees of hold, which are not only intensified by the use of the esters described below but are supplemented by an excellent hair feel. Hair sprays preferred according to the invention are therefore characterized in that the aerosol composition includes, based on its weight, 0.1 to 10% by weight, preferably 0.25 to 9% by weight, more preferably 0.5 to 8% by weight, particularly preferably 0.75 to 7% by weight, and particularly 1 to 6% by weight of copolymer(s) of N-octylacrylamide/acrylic acid/tert-butylaminoethyl methacrylate (INCI name: Octylacrylamide/Acrylates/Butylaminoethyl Methacrylate Copolymer).

The hair spray compositions of the invention include as the third essential component 0.01 to 5% by weight of esters of the formula (I)

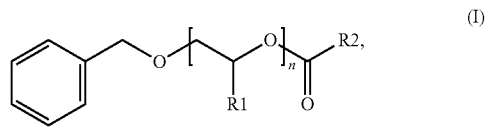

in which

R1 stands for —H or —$CH_3$,

R2 for a straight-chain or branched alkyl group having 7 to 15 carbon atoms, and n for an integer from the group comprising 1, 2, 3, 4, 5, 6, 7, 8.

Preferably, the ester(s) of the formula (I) is (are) used within rather narrow amount ranges. Preferred hair sprays are characterized in that the aerosol composition includes, based on its weight, 0.11 to 4.5% by weight, preferably 0.12 to 4% by weight, more preferably 0.13 to 3% by weight, particularly preferably 0.14 to 2.5% by weight, and particularly 0.15 to 2% by weight of esters of the formula (I).

In formula (I), R1 preferably stands for a methyl group, so that preferred hair sprays are characterized in that the aerosol composition includes, based on its weight, 0.11 to 4.5% by weight, preferably 0.12 to 4% by weight, more preferably 0.13 to 3% by weight, particularly preferably 0.14 to 2.5% by weight, and particularly 0.15 to 2% by weight of esters of the formula (Ia)

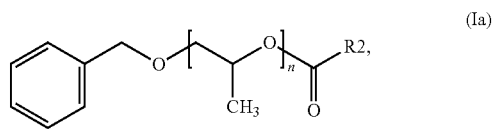

in which

R2 stands for a straight-chain or branched alkyl group having 7 to 15 carbon atoms, and n for an integer from the group comprising 1, 2, 3, 4, 5, 6, 7, 8.

In formula (Ia), n preferably stands for an integer from the group comprising 1, 2, 3, 4, 5, 6; i.e., preferred esters can be described by the formulas (Ia-1) to (Ia-6):

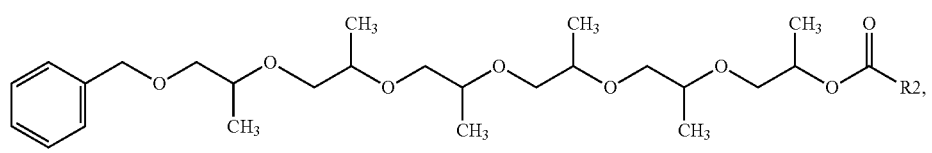
(Ia-1)

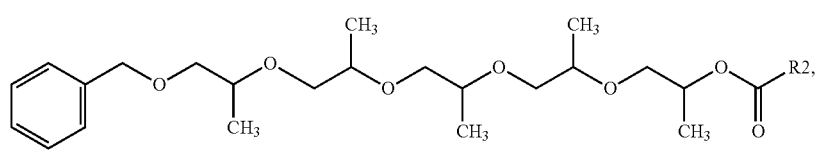
(Ia-2)

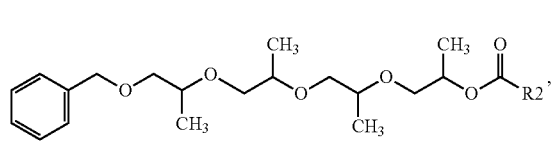
(Ia-3)

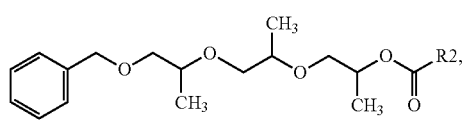
(Ia-4)

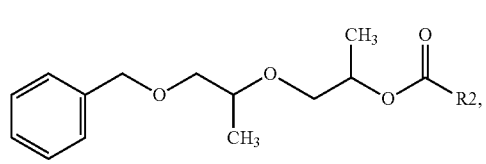
(Ia-5)

(Ia-6)

in which R2 in each case stands for a straight-chain or branched alkyl group having 7 to 15 carbon atoms.

Very particularly preferred groups R2 stand for tridecyl or ethylhexyl groups, so that particularly preferred hair sprays are characterized in that the aerosol composition includes, based on its weight, 0.11 to 4.5% by weight, preferably 0.12 to 4% by weight, more preferably 0.13 to 3% by weight, particularly preferably 0.14 to 2.5% by weight, and particularly 0.15 to 2% by weight of esters of the formula (Ib)

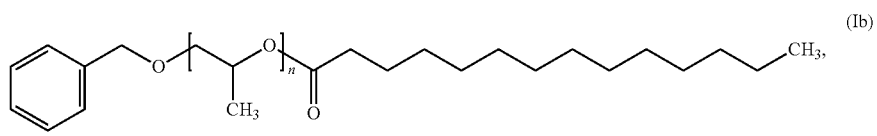
(Ib)

in which n stands for an integer from the group comprising 1, 2, 3, or 4, preferably for 2 or 3, and particularly for 3, and other likewise particularly preferred hair sprays are characterized in that the aerosol composition includes, based on its weight, 0.11 to 4.5% by weight, preferably 0.12 to 4% by weight, more preferably 0.13 to 3% by weight, particularly preferably 0.14 to 2.5% by weight, and particularly 0.15 to 2% by weight of esters of the formula (Ic)

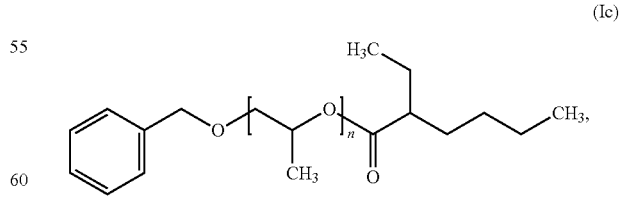
(Ic)

in which n stands for an integer from the group comprising 1, 2, 3, or 4, preferably for 2 or 3, and particularly for 3. Esters to be used with very particular preference are accordingly the compounds (Ib-1) and (Ic-1):

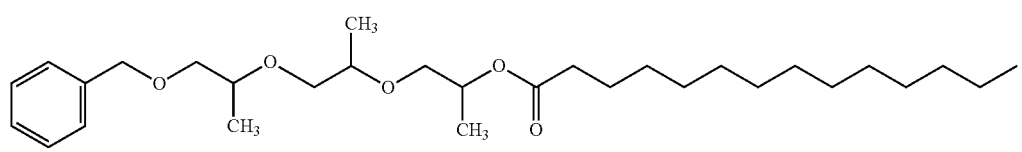

(Ib-1)

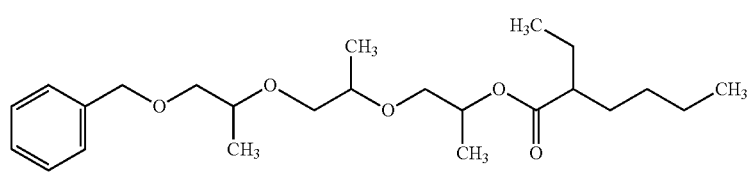

(Ic-1)

In addition to the above-described copolymers and esters, the cosmetic agents of the invention can include further ingredients. The group of these further ingredients includes in particular cosmetically active auxiliary substances and additives.

The cosmetic agents of the invention include as a preferred component at least one quaternary ammonium compound. Monomeric or polymeric active substances can be used as the quaternary ammonium compound.

Of the many possible monomeric quaternary ammonium compounds, compounds from the groups:

trimethylalkylammonium halides, esterquats, quaternary imidazolines have proven to be especially effective.

The group of trimethylalkylammonium halides includes in particular compounds of the formula (Tkat1-1).

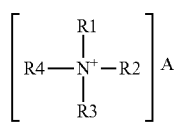

(Tkat1)

In the formula (Tkat1), R1, R2, R3, and R4 in each case independently of one another stand for hydrogen, a methyl group, a phenyl group, a benzyl group, for a saturated, branched or unbranched alkyl group having a chain length of 8 to 30 carbon atoms, which optionally can be substituted with one or more hydroxy groups. "A" stands for a physiologically acceptable anion, for example, halides such as chloride or bromide and methosulfates.

Examples of compounds of the formula (Tkat1) are lauryl trimethyl ammonium chloride, cetyl trimethyl ammonium chloride, cetyl trimethyl ammonium bromide, cetyl trimethyl ammonium methosulfate, dicetyl dimethyl ammonium chloride, tricetyl methyl ammonium chloride, stearyl trimethyl ammonium chloride, distearyl dimethyl ammonium chloride, lauryl dimethyl benzyl ammonium chloride, behenyl trimethyl ammonium chloride, behenyl trimethyl ammonium bromide, and behenyl trimethyl ammonium methosulfate. Preferred cosmetic agents include a monomeric quaternary ammonium compound from the group of trimethyl alkyl ammonium halides.

Other quaternary ammonium compounds particularly preferred according to the invention are the cationic betaine esters of the formula (Tkat1-2.1).

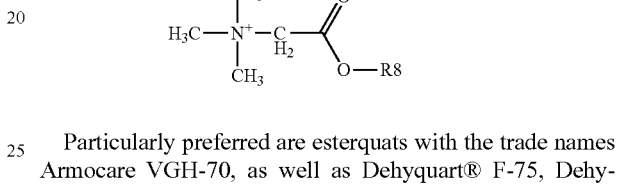

(Tkat1-2.1)

Particularly preferred are esterquats with the trade names Armocare VGH-70, as well as Dehyquart® F-75, Dehyquart® L80, Stepantex® VS 90, and Akypoquat® 131.

Another group constitutes quaternary imidazoline compounds. The formula (Tkat2) illustrated below shows the structure of these compounds.

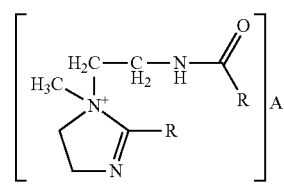

(Tkat2)

The R groups independently of one another each stand for a saturated or unsaturated, linear or branched hydrocarbon group with a chain length of 8 to 30 carbon atoms. The preferred compounds of the formula (Tkat2) include in each case the same hydrocarbon group for R. The chain length of the R groups is preferably 12 to 21 carbon atoms. "A" stands for an anion as described previously. Particularly inventive examples are obtainable, for example, under the INCI names: Quaternium-27, Quaternium-72, Quaternium-83, Quaternium-87, and Quaternium-91. Quaternium-91 is most preferable according to the invention. In regard to the cosmetic action, cosmetic agents have proven advantageous in which the percentage by weight of the monomeric quaternary ammonium compound relative to the total weight of the agent is 0.05 to 3.0% by weight, preferably 0.1 to 2.0% by weight, and particularly 0.2 to 1.0% by weight.

Additional care substances can be named in particular as suitable auxiliary substances and additives.

The agent can include as a care substance of a different compound class, for example, at least one protein hydrolysate and/or a derivative thereof. Protein hydrolysates are product mixtures obtained by acid-, base-, or enzyme-catalyzed degradation of proteins. The term protein hydrolysates according to the invention is also understood to be total hydrolysates, as well as individual amino acids and derivatives thereof, and mixtures of different amino acids.

The molar weight of protein hydrolysates usable according to the invention is between 75, the molar weight of glycine, and 200,000; the molar weight is preferably 75 to 50,000 daltons, and very especially preferred 75 to 20,000 daltons.

The agent according to the invention can include as a care substance further at least one vitamin, provitamin, vitamin precursor, and/or a derivative thereof. The vitamins, provitamins, and vitamin precursors usually assigned to groups A, B, C, E, F, and H are preferred according to the invention.

Like the addition of glycerol and/or propylene glycol, the addition of panthenol increases the flexibility of the polymer film formed during use of the agent according to the invention.

The agents of the invention, furthermore, can include as a care substance at least one plant extract but also mono- or oligosaccharides and/or lipids.

Furthermore, oil components are suitable as a care substance. Natural and synthetic cosmetic oil components include, for example, plant oils, liquid paraffin oils, isoparaffin oils, and synthetic hydrocarbons, as well as di-n-alkyl ethers having a total of 12 to 36 C atoms, especially 12 to 24 C atoms. Preferred cosmetic agents of the invention include at least one oil component, preferably at least one oil component from the group of silicone oils. The group of silicone oils comprises in particular dimethicones, which also include cyclomethicones, amino-functional silicones, as well as dimethiconols. Dimethicones can be both linear and branched, as well as cyclic or cyclic and branched. Suitable silicone oils or silicone gums are, in particular, dialkyl- and alkylarylsiloxanes, such as, for example, dimethylpolysiloxane and methylphenylsiloxane, as well as alkoxylated, quaternized, or also anionic derivatives thereof. Cyclic and linear polydialkylsiloxanes, alkoxylated and/or aminated derivatives thereof, dihydroxypolydimethylsiloxanes, and polyphenylalkylsiloxanes are preferred.

Further preferred nourishing oil components are ester oils, i.e., esters of $C_6$-$C_{30}$ fatty acids with $C_2$-$C_{30}$ fatty alcohols, preferably monoesters of fatty acids with alcohols having 2 to 24 C atoms, such as, for example, isopropyl myristate (Rilanit® IPM), isononanoic acid C16-18 alkyl esters (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V).

Suitable as care substances, furthermore, are dicarboxylic acid esters, symmetric, asymmetric, or cyclic esters of carbonic acid with fatty alcohols, tri-fatty acid esters of saturated and/or unsaturated, linear and/or branched fatty acids with glycerol, or fatty acid partial glycerides, which are understood to be monoglycerides, diglycerides, and technical mixtures thereof. In regard to the cosmetic action, cosmetic agents have proven advantageous in which the percentage by weight of the oil component relative to the total weight of the agent is 0.01 to 5.0% by weight, preferably 0.02 to 4.0% by weight, and particularly 0.05 to 2.0% by weight.

The combination of the invention comprises furthermore a dispenser (pressurized container), from which the propellant gas-containing hair treatment agent, contained therein, is sprayed out with the aid of the propellant. According to the invention, the dispenser preferably comprises a valve, which has a valve opening, which is designed as a taper bore and whose diameter is maximum of 0.4 mm. In addition, the valve preferably has a throttle, which has a maximum inside diameter of 0.3 mm, but no side bore ("gas phase bore"). Preferably, the diameter of the taper bore as well is 0.15 to 0.4 mm, preferably 0.175 to 0.375 mm, more preferably 0.2 to 0.35 mm, and particularly 0.25 to 0.3 mm. Preferably, the depth of the taper bore is a maximum of 0.3 mm. Preferred combinations of the invention are characterized further in that the depth of the taper bore is 0.1 to 0.3 mm, preferably 0.125 to 0.275 mm, more preferably 0.15 to 0.25 mm, and particularly 0.2 to 0.25 mm.

The valve design comprises furthermore preferably a throttle, which limits the throughput. The throttle is located in this case either in the valve stem or in the spray head. Said throttle in preferred embodiments of the present invention has an inside diameter of 0.1 to 0.3 mm, preferably 0.125 to 0.275 mm, more preferably 0.15 to 0.25 mm, and particularly 0.2 to 0.25 mm. The compositions of the invention can be packaged in commercial aerosol containers. The containers can be made of tin plate or of aluminum. Furthermore, the containers can be coated on the inside to keep the risk of corrosion as low as possible. The use of inner pouches in containers as well is easily possible. The containers are equipped with a suitable spray head. Depending on the spray head, discharge rates, based on fully filled containers, of 0.1 g/s to 5.0 g/s are possible.

A further subject matter of the present invention is a method for styling hair, in which an aerosol composition, including esters of the formula (I)

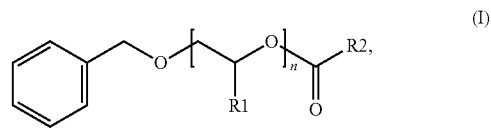

in which

R1 stands for —H or —CH$_3$,

R2 for a straight-chain or branched alkyl group having 7 to 15 carbon atoms, and n for an integer from the group comprising 1, 2, 3, 4, 5, 6, 7, 8, is applied to keratinic fibers by means of a propellant or a propellant mixture from a pressurized container.

Preferred methods of the invention therefore use the esters in combination with at least one fixing polymer. The statements made regarding the agent of the invention also apply mutatis mutandis to other preferred embodiments of the method of the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair spray, comprising a pressurized container and, located therein, an aerosol composition, which includes, based on the total weight of the aerosol composition,
   a) 20 to 80% by weight of at least one propellant,
   b) 0.1 to 20% by weight of at least one fixing polymer,
   c) 0.11 to 4.5% by weight of esters of the formula (Ib),

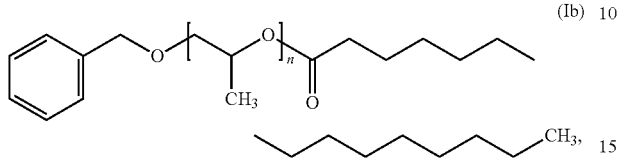

in which n stands for an integer from the group comprising 1, 2, 3, or 4.

2. The hair spray according to claim 1, wherein the aerosol composition includes 20 to 80% by weight, based on the total weight of the composition, of a propellant or propellant mixture.

3. The hair spray according to claim 1, wherein the aerosol composition includes 27.5 to 72.5% by weight, based on the total weight of the composition, of a propellant or propellant mixture.

4. The hair spray according to claim 1, wherein the aerosol composition includes one or more propellant selected form the group consisting of dimethyl ether, HFO1234yf, HFO1234ze, propane, propene, n-butane, isobutane, isobutene, n-pentane, pentene, isopentane, and isopentene.

5. The hair spray according to claim 1, wherein the propellant includes dimethyl ether and one or more compound selected from the group consisting of propane, propene, n-butane, isobutane, isobutene, n-pentane, pentene, isopentane, isopentene, dimethyl ether.

6. The hair spray according to claim 1, wherein the fixing polymer comprises 0.2% by weight to 17.5% of the aerosol composition.

7. The hair spray according to claim 1, wherein the fixing polymer comprises 0.5% by weight to 15% by weight of the aerosol composition.

8. The hair spray according to claim 1, wherein the fixing polymer includes at least one nonionic polymer based on ethylenically unsaturated monomers.

9. The hair spray according to claim 1, wherein the fixing polymer includes at least one polymer selected from the group consisting of: homopolymers of N-vinylpyrrolidone, nonionic copolymers of N-vinylpyrrolidone, homopolymers and nonionic copolymers of N-vinylcaprolactam, copolymers of (meth)acrylamide, polyvinyl alcohol, polyvinyl acetate, chitosan and cellulose derivatives, cationic copolymers of 3-($C_1$ to $C_6$)-alkyl-1-vinyl imidazolinium, homopolymers and copolymers including the structural unit of the formula (M-1)

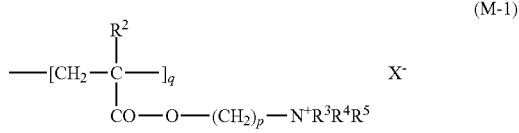

in which $R^2$=—H or —$CH_3$, $R^3$, $R^4$, and $R^5$ independently of one another are selected from ($C_1$ to $C_4$) alkyl, ($C_1$ to $C_4$) alkenyl, or ($C_2$ to $C_4$) hydroxyalkyl groups, p=1, 2, 3, or 4, q is a natural number, and $X^-$ is a physiologically acceptable organic or inorganic anion, anionic polymers which have carboxylate and/or sulfonate groups, and anionic polyurethanes.

10. The hair spray according to claim 1, wherein the aerosol composition includes at least one film-forming and/or fixing polymer selected from the group consisting of:
   aminomethyl propanol salts of copolymers of allyl methacrylate with one or more monomers selected from acrylic acid, methacrylic acid, acrylic acid esters, and methacrylic acid esters,
   vinylpyrrolidone/vinyl acetate copolymers,
   vinylpyrrolidone/vinylcaprolactam/dimethylaminopropyl-acrylamide copolymers,
   copolymers of octylacrylamide with t-butylaminoethyl methacrylate and two or more monomers selected from acrylic acid, methacrylic acid, acrylic acid esters, and methacrylic acid esters, and
   copolymers of $C_{1-2}$-alkyl succinates with hydroxyalkyl acrylates and one or more monomers selected from acrylic acid, methacrylic acid, acrylic acid esters, and methacrylic acid esters.

11. The hair spray according to claim 1, wherein the aerosol composition includes as a fixing polymer an aminomethyl propanol salt of a copolymer of allyl methacrylate with one or more monomers, selected from acrylic acid, methacrylic acid, acrylic acid esters, and methacrylic acid esters.

12. The hair spray according to claim 1, wherein the aerosol composition includes, based on its weight, 0.1 to 10% by weight copolymer(s) of N-octylacrylamide/acrylic acid/tert-butylaminoethyl methacrylate (INCI name: Octylacrylamide/Acrylates/Butylaminoethyl Methacrylate Copolymer).

13. A method for styling hair, comprising applying to keratinic fibers an aerosol composition including, based on the total weight of the aerosol composition, 0.11 to 4.5% by weight of esters of the formula (Ib)

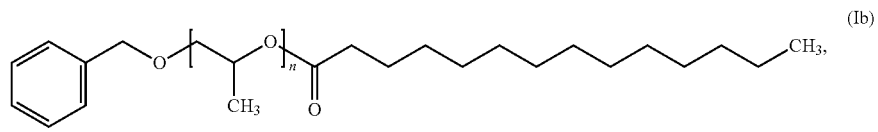

in which n stands for an integer from the group comprising 1, 2, 3, or 4.

* * * * *